(12) United States Patent
Kopkalli et al.

(10) Patent No.: US 11,555,001 B2
(45) Date of Patent: Jan. 17, 2023

(54) METHOD FOR DEHYDROCHLORINATION OF HCFC-244BB TO MANUFACTURE HFO-1234YF

(71) Applicant: HONEYWELL INTERNATIONAL INC., Morris Plains, NJ (US)

(72) Inventors: Haluk Kopkalli, Morris Plains, NJ (US); Carlos Navar, Morris Plains, NJ (US); Yuon Chiu, Morris Plains, NJ (US); Haiyou Wang, Morris Plains, NJ (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 16/972,473

(22) PCT Filed: Jun. 5, 2019

(86) PCT No.: PCT/US2019/035609
§ 371 (c)(1),
(2) Date: Dec. 4, 2020

(87) PCT Pub. No.: WO2019/236720
PCT Pub. Date: Dec. 12, 2019

(65) Prior Publication Data
US 2021/0163383 A1    Jun. 3, 2021

Related U.S. Application Data

(63) Continuation-in-part of application No. 16/001,728, filed on Jun. 6, 2018, now abandoned.

(51) Int. Cl.
*C07C 17/25* (2006.01)
*C07C 17/38* (2006.01)
*C07C 17/383* (2006.01)

(52) U.S. Cl.
CPC .............. *C07C 17/25* (2013.01); *C07C 17/38* (2013.01); *C07C 17/383* (2013.01)

(58) Field of Classification Search
CPC ..................................................... C07C 17/25
See application file for complete search history.

(56) References Cited

U.S. PATENT DOCUMENTS 2,427,116 A    9/1947  Barrick
2,441,128 A    5/1948  Barrick et al.
(Continued)

FOREIGN PATENT DOCUMENTS

CN    101913989 B  *  6/2013
GB      2547277 A      8/2017
(Continued)

OTHER PUBLICATIONS

Translation of CN101913989B, Jun. 2013, pp. 1-10 (Year: 2013).*
(Continued)

*Primary Examiner* — Medhanit W Bahta
(74) *Attorney, Agent, or Firm* — Faegre Drinker Biddle & Reath LLP

(57) ABSTRACT

A process for making 2,3,3,3-tetrafluoropropene (HFO-1234yf) includes providing a composition including 2-chloro-1,1,1,2-tetrafluoropropane (HCFC-244bb) to a reactor including a heater surface at a surface temperature greater than about 850° F. (454° C.), and then bringing the composition into contact with the heater surface for a contact time of less than 10 seconds to dehydrochlorinate a portion of the HCFC-244bb to make HFO-1234yf.

10 Claims, 2 Drawing Sheets

(56) References Cited

U.S. PATENT DOCUMENTS

| | | |
|---|---|---|
| 2,462,345 A | 2/1949 | Barrick |
| 2,848,504 A | 8/1958 | Dixon |
| 2,931,840 A | 4/1960 | Marquis |
| 2,982,786 A | 5/1961 | McCane |
| 3,484,502 A | 12/1969 | McCarthy |
| 3,996,299 A | 12/1976 | Fozzard |
| 3,996,301 A | 12/1976 | Fozzard |
| 4,086,407 A | 4/1978 | Fozzard |
| 4,413,041 A | 11/1983 | Hegedus |
| 4,900,874 A | 2/1990 | Ihara et al. |
| 5,026,499 A | 6/1991 | Merchant |
| 5,035,830 A | 7/1991 | Merchant |
| 5,162,594 A | 11/1992 | Krespan |
| 5,895,639 A | 4/1999 | Swain et al. |
| 5,902,912 A | 5/1999 | Tung et al. |
| 6,624,337 B1 | 9/2003 | Manzer et al. |
| 7,135,601 B2 | 11/2006 | Mukhopadhyay et al. |
| 7,674,939 B2 | 3/2010 | Mukhopadhyay et al. |
| 8,058,486 B2 | 11/2011 | Merkel et al. |
| 8,084,653 B2 | 12/2011 | Tung et al. |
| 8,324,436 B2 | 12/2012 | Mukhopadhyay et al. |
| 8,425,795 B2 | 4/2013 | Nappa et al. |
| 8,481,793 B2 | 7/2013 | Merkel et al. |
| 8,618,340 B2 | 12/2013 | Kopkalli et al. |
| 8,766,020 B2 | 7/2014 | Wang et al. |
| 8,975,454 B2 | 3/2015 | Merkel et al. |
| 9,061,957 B2 | 6/2015 | Mukhopadhyay et al. |
| 9,463,432 B2 | 10/2016 | Tung et al. |
| 9,790,151 B2 | 10/2017 | Banavali et al. |
| 9,790,152 B2 | 10/2017 | Sharratt et al. |
| 9,856,193 B2 | 1/2018 | Nair et al. |
| 10,005,705 B2 | 6/2018 | Nair et al. |
| 10,071,940 B2 | 9/2018 | Banavali et al. |
| 2006/0217577 A1 | 9/2006 | Mukhopadhyay et al. |
| 2007/0096053 A1 | 5/2007 | Nair et al. |
| 2007/0112230 A1 | 5/2007 | Mukhopadhyay et al. |
| 2007/0179324 A1 | 8/2007 | Van et al. |
| 2007/0197842 A1 | 8/2007 | Mukhopadhyay et al. |
| 2008/0058562 A1 | 3/2008 | Petrov et al. |
| 2008/0207962 A1 | 8/2008 | Rao et al. |
| 2009/0043136 A1 | 2/2009 | Wang et al. |
| 2009/0099396 A1 | 4/2009 | Mukhopadhyay et al. |
| 2009/0186986 A1 | 7/2009 | Nomura et al. |
| 2009/0211988 A1 | 8/2009 | Pham et al. |
| 2009/0240090 A1 | 9/2009 | Merkel et al. |
| 2009/0242832 A1 | 10/2009 | Pham et al. |
| 2009/0287026 A1 | 11/2009 | Kopkalli et al. |
| 2009/0287027 A1 | 11/2009 | Merkel et al. |
| 2010/0022808 A1 | 1/2010 | Rao et al. |
| 2010/0029997 A1 | 2/2010 | Wang et al. |
| 2010/0036179 A1 | 2/2010 | Merkel et al. |
| 2010/0048961 A1 | 2/2010 | Merkel et al. |
| 2010/0187088 A1 | 7/2010 | Merkel et al. |
| 2010/0210882 A1 | 8/2010 | Sharratt et al. |
| 2010/0305370 A1 | 12/2010 | Devic et al. |
| 2011/0097529 A1 | 4/2011 | Durali et al. |
| 2011/0237846 A1 | 9/2011 | Kawaguchi et al. |
| 2012/0065437 A1* | 3/2012 | Merkel ............... B01D 3/10 570/175 |
| 2012/0184785 A1 | 7/2012 | Cottrell et al. |
| 2012/0296128 A1 | 11/2012 | Merkel et al. |
| 2014/0147480 A1 | 5/2014 | Lu et al. |
| 2014/0179887 A1 | 6/2014 | Lu et al. |
| 2014/0235903 A1 | 8/2014 | Wang et al. |
| 2015/0183698 A1 | 7/2015 | Merkel et al. |
| 2015/0259266 A1 | 9/2015 | Takahashi et al. |
| 2017/0137353 A1 | 5/2017 | Banavali et al. |
| 2017/0233316 A1 | 8/2017 | Nair et al. |

FOREIGN PATENT DOCUMENTS

| | | |
|---|---|---|
| JP | 2012-188359 A | 10/2012 |
| KR | 10-2011-0093831 A | 8/2011 |
| WO | 97/37955 A1 | 10/1997 |
| WO | 97/38958 A1 | 10/1997 |
| WO | 00/75092 A1 | 12/2000 |
| WO | 2005/037743 A1 | 4/2005 |
| WO | 2006/011868 A1 | 2/2006 |
| WO | 2007/056194 A1 | 5/2007 |
| WO | 2007/058836 A2 | 5/2007 |
| WO | 2007/079431 A2 | 7/2007 |
| WO | 2007/117391 A1 | 10/2007 |
| WO | 2008/002499 A2 | 1/2008 |
| WO | 2008/002501 A2 | 1/2008 |
| WO | 2008/012559 A1 | 1/2008 |
| WO | 2008/030440 A2 | 3/2008 |
| WO | 2008/057794 A1 | 5/2008 |
| WO | 2008/060612 A2 | 5/2008 |
| WO | 2008/075017 A2 | 6/2008 |
| WO | 2009/003085 A1 | 12/2008 |
| WO | 2009/084703 A1 | 7/2009 |
| WO | 2009/093047 A2 | 7/2009 |
| WO | 2009/125199 A2 | 10/2009 |
| WO | 2010/013796 A1 | 2/2010 |
| WO | 2010/055146 A2 | 5/2010 |
| WO | 2011-130108 A1 | 10/2011 |
| WO | 2012-006295 A1 | 1/2012 |
| WO | 2013-071024 A1 | 5/2013 |
| WO | 2017/013405 A1 | 1/2017 |
| WO | 2017-066603 A1 | 4/2017 |
| WO | 2017/083318 A1 | 5/2017 |

OTHER PUBLICATIONS

Banks et al., "Preparation of 2,3,3,3-tetrafluoropropene from trifluoroacetylacetone and sulphur tetrafluoride", Journal of Fluorine Chemistry, vol. 82, pp. 171-174 (1997).

Birchall, Michael J., et al. "Cyclopropane Chemistry. Part III. Thermal Decomposition of Some Halogenopolyfluorocyclopropanes." Journal of the Chemical Society, Perkin Transactions 1: Organic and Bio-Organic Chemistry, 16:1773-1779, 1973.

Hauptschein, Murray, et al. "The Thermal Dimerization of Perfluoropropene." Contribution from the Organic Research Department, Pennsalt Chemicals Corp., vol. 80, pp. 842-845, Feb. 20, 1958.

International Search Report and Written Opinion issued in PCT/US2016/061021, dated Jan. 17, 2017, 7 pages.

International Search Report and Written Opinion issued in PCT/US2017/060394, dated Feb. 14, 2018, 11 pages.

International Search Report and Written Opinion received for PCT Patent Application No. PCT/US2019/035609, dated Sep. 20, 2019, 9 pages.

Knuayants, I. L. et al., "Reactions to Fluoro Olefins. XIII. Catalytic Hydrogenation of Perfluoro Olefins", English translation, Institute of Heteroorganic Compounds, Academy of Sciences of the USSR, No. 8, pp. 1412-1418, Aug. 1960.

Lu et al., production method of 2,3,3,3-tetrafluoropropene, (CN 101913989 Machine translation), Dec. 2010.

Placzek, D. W. and Rabinovitch, B.S. "The Thermal Isomerization of Trifluoromethyl- and Trifluoroethylcyclopropane." The Journal of Physical Chemistry, 69(7):2141-2145, Jul. 2015, 1965.

Sakaino, Yoshiko. "Structures and Chromotropic Properties of Imadazole Derivatives Produced from 3,6-Bis(4,5-diphenyl-2H-imidazol-2-ylidene)cyclohexa-1,4-diene."J. Chem. Soc. Perkin Trans. I, pp. 1063-1066, 1983.

Solvay Solexis, Via S. Pietro. "2Pi Plus 2Pi Cycloaddition Kinetics of Some Fluoro Olefins and Fluoro Vinyl Ethers." Elsevier, Journal of Fluorine Chemistry, 125:1519-1528, 2004.

Stoiljkovich, D. and Jovanovich, S. "The Mechanism of the High-Pressure Free Radical Polymerization of Ethylene." Journal of Polymer Science: Polymer Chemistry Edition, vol. 19, 741-747, 1981.

US. Appl. filed Nov. 2, 2016, 17 pages, U.S. Appl. No. 62/416,206.

\* cited by examiner

METHOD FOR DEHYDROCHLORINATION OF HCFC-244BB TO MANUFACTURE HFO-1234YF

FIELD

The present disclosure relates to methods for manufacturing 2,3,3,3-tetrafluoropropene (HFO-1234yf). Specifically, the present disclosure relates to methods for the dehydrochlorination of 2-chloro-1,1,1,2-tetrafluoropropane (HCFC-244bb) in the manufacture of HFO-1234yf.

BACKGROUND

Hydrofluoroolefins (HFOs), such as tetrafluoropropenes are known effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Due to suspected environmental problems associated with the use of some of these fluids, including the relatively high global warming potentials associated therewith, it is desirable to use fluids having the lowest possible global warming potential (GWP) in addition to also having zero ozone depletion potential (ODP). Thus, there is considerable interest in developing environmentally friendlier materials for the applications mentioned above.

HFOs having zero ozone depletion and low global warming potential have been identified as potentially filling this need. However, the toxicity, boiling point, and other physical properties of such chemicals vary greatly from isomer to isomer. One HFO having valuable properties is 2,3,3,3-tetrafluoropropene (HFO-1234yf or 1234yf).

HFO-1234yf has been shown to be a low global warming compound with low toxicity and, thus, can meet increasingly stringent requirements for refrigerants in mobile air conditioning. Accordingly, compositions containing 1234yf are among the materials being developed for use in many applications.

SUMMARY

The present disclosure provides a process for making 2,3,3,3-tetrafluoropropene (HFO-1234yf) includes providing a composition including 2-chloro-1,1,1,2-tetrafluoropropane (HCFC-244bb) to a reactor including a heater surface at a surface temperature greater than about 850° F. (454° C.), and then bringing the composition into contact with the heater surface for a contact time of less than 10 seconds to dehydrochlorinate a portion of the HCFC-244bb to make HFO-1234yf.

In one form thereof, the present disclosure provides a process for making 2,3,3,3-tetrafluoropropene (HFO-1234yf), the process including providing a composition including 2-chloro-1,1,1,2-tetrafluoropropane (HCFC-244bb) to a reactor including a heater surface at a surface temperature greater than about 850° F. (454° C.), and bringing the composition into contact with the heater surface for a contact time of less than 10 seconds to dehydrochlorinate a portion of the HCFC-244bb to make HFO-1234yf.

The heater surface may be at a surface temperature from about 870° F. (466° C.) to about 1,200° F. (649° C.). The contact time may be from 0.1 seconds to 9 seconds. In some embodiments, the heater surface may include a catalytic surface. The catalytic surface may include electroless nickel, nickel, stainless steel, nickel-copper alloy, nickel-chromium-iron alloy, nickel-chromium alloy, nickel-chromium-molybdenum, or combinations thereof. In other embodiments, the heater surface may not be a catalytic surface.

The process may further include vaporizing the composition, and then heating the vaporized composition to a temperature from about 575° F. (302° C.) to 1,200° F. (649° C.) before providing the composition to the reactor. The process may further include providing the HFO-1234yf, HCl, and unreacted HCFC-244bb from the reactor to a distillation column, separating the HFO-1234yf and the HCl from at least a portion of the HCFC-244bb in the distillation column, recycling the separated HCFC-244bb into the composition before vaporizing the composition, providing the HFO-1234yf and the HCl to an HCl separation unit, and separating the HCl from the HFO-1234yf to form a product stream including the HFO-1234yf. The product stream may include the HFO-1234yf at a concentration greater than 99.1 wt. % on an HCFC-244bb-free basis. The product stream may further include 1,1,1,2-tetrafluoroethane at a concentration less than 0.1 wt. % on an HCFC-244bb-free basis as an indication of a low rate of carbon build-up in the reactor. Heating the vaporized composition may include exchanging heat between the vaporized composition and the HFO-1234yf and HCFC-244bb from the reactor before providing the HFO-1234yf and HCFC-244bb to the distillation column.

In another form thereof, the present disclosure provides a process for a process for making 2,3,3,3-tetrafluoropropene (HFO-1234yf), the process including vaporizing a composition including 2-chloro-1,1,1,2-tetrafluoropropane (HCFC-244bb), dividing the composition into a first portion and a second portion, heating the first portion of the vaporized composition to a temperature from about 575° F. (302° C.) to 1,200° F. (649° C.), providing the composition to a reactor including a heater surface at a surface temperature greater than about 850° F. (454° C.), and bringing the composition into contact with the heater surface for a contact time of less than 10 seconds to dehydrochlorinate a portion of the HCFC-244bb to make HFO-1234yf. The reactor can include a first stage and a second stage downstream from the first stage. The first portion can be provided to the first stage and the second portion can be provided to the second stage.

The process may further include providing the HFO-1234yf, HCl, and unreacted HCFC-244bb from the reactor to a distillation column, separating the HFO-1234yf and the HCl from at least a portion of the HCFC-244bb in the distillation column, recycling the separated HCFC-244bb into the composition before vaporizing the composition, providing the HFO-1234yf and the HCl to an HCl separation unit, and separating the HCl from the HFO-1234yf to form a product stream including the HFO-1234yf. The product stream may include the HFO-1234yf at a concentration greater than 99.1 wt. % on an HCFC-244bb-free basis. The product stream may further include 1,1,1,2-tetrafluoroethane at a concentration less than 0.1 wt. % on an HCFC-244bb-free basis as an indication of a low rate of carbon build-up in the reactor.

Heating the first portion of the vaporized composition may include exchanging heat between the first portion of the vaporized composition and the HFO-1234yf and HCFC-244bb from the reactor before providing the HFO-1234yf and HCFC-244bb to the distillation column. The heater surface may be at a surface temperature from about 870° F. (466° C.) to about 1,200° F. (649° C.). The contact time may be from 0.1 seconds to 9 seconds. The heater surface may include a catalytic surface. The heater surface may not be a catalytic surface.

The above mentioned and other features of the disclosure, and the manner of attaining them, will become more apparent and will be better understood by reference to the following description of embodiments taken in conjunction with the accompanying drawings.

DETAILED DESCRIPTION

Various methods are known for producing HFO-1234yf, such as those described in U.S. Pat. No. 8,058,486, entitled INTEGRATED PROCESS TO PRODUCE 2,3,3,3-TETRAFLUOROPROPENE issued on Nov. 15, 2011, U.S. Pat. No. 8,975,454, entitled PROCESS FOR PRODUCING 2,3,3,3-TETRAFLUOROPROPENE issued on Mar. 10, 2015, and U.S. Pat. No. 8,766,020, entitled PROCESS FOR PRODUCING 2,3,3,3-TETRAFLUOROPROPENE issued on Jul. 1, 2014, all of which are herein incorporated by reference in their entirety.

The manufacture of HFO-1234yf from 1,1,2,3-tetrachloropropene (HCO-1230xa, or 1230xa) and hydrogen fluoride can be generalized in a three-step process. Step 1 can be understood as producing 2-chloro-3,3,3-trifluoropropene (HCFO-1233xf, or 1233xf) from 1230xa in a vapor phase reactor according to the following reaction scheme:

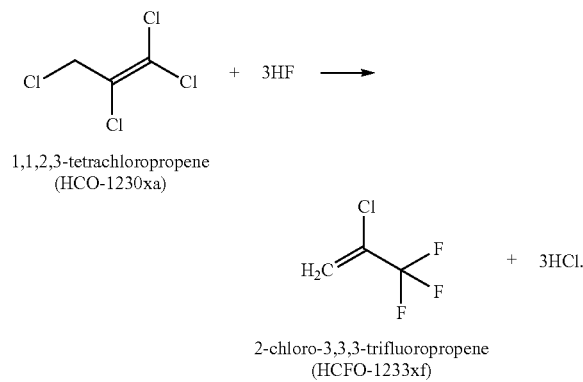

1,1,2,3-tetrachloropropene
(HCO-1230xa)

2-chloro-3,3,3-trifluoropropene
(HCFO-1233xf)

Step 2 can be understood as producing 2-chloro-1,1,1,2-tetrafluoropropane (HCFC-244bb or 244bb) from 1233xf in a reactor, such as a liquid phase reactor, according to the following reaction scheme:

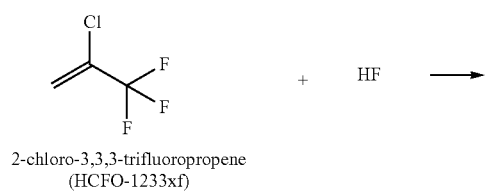

2-chloro-3,3,3-trifluoropropene
(HCFO-1233xf)

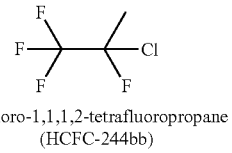

2-chloro-1,1,1,2-tetrafluoropropane
(HCFC-244bb)

Step 3 can be understood as a dehydrochlorination reaction producing 2,3,3,3-tetrafluoropropene (HFO-1234yf) from 2-chloro-1,1,1,2-tetrafluoropropane (HCFC-244bb) in a reactor, such as a vapor phase reactor according to the following reaction scheme:

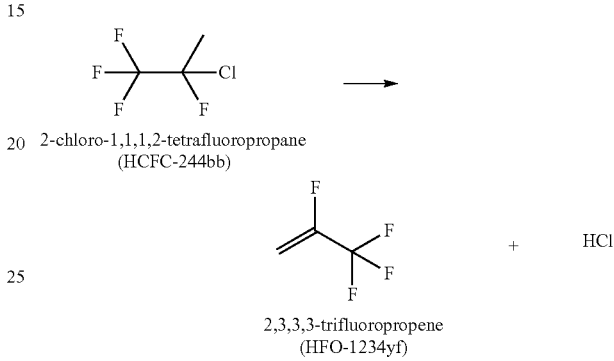

2-chloro-1,1,1,2-tetrafluoropropane
(HCFC-244bb)

2,3,3,3-trifluoropropene
(HFO-1234yf)

More specifically, the balanced equation for Step 3 can be:

$$244bb \rightarrow 1234yf + HCl \qquad \text{Eq. 1}$$

Figure 1:
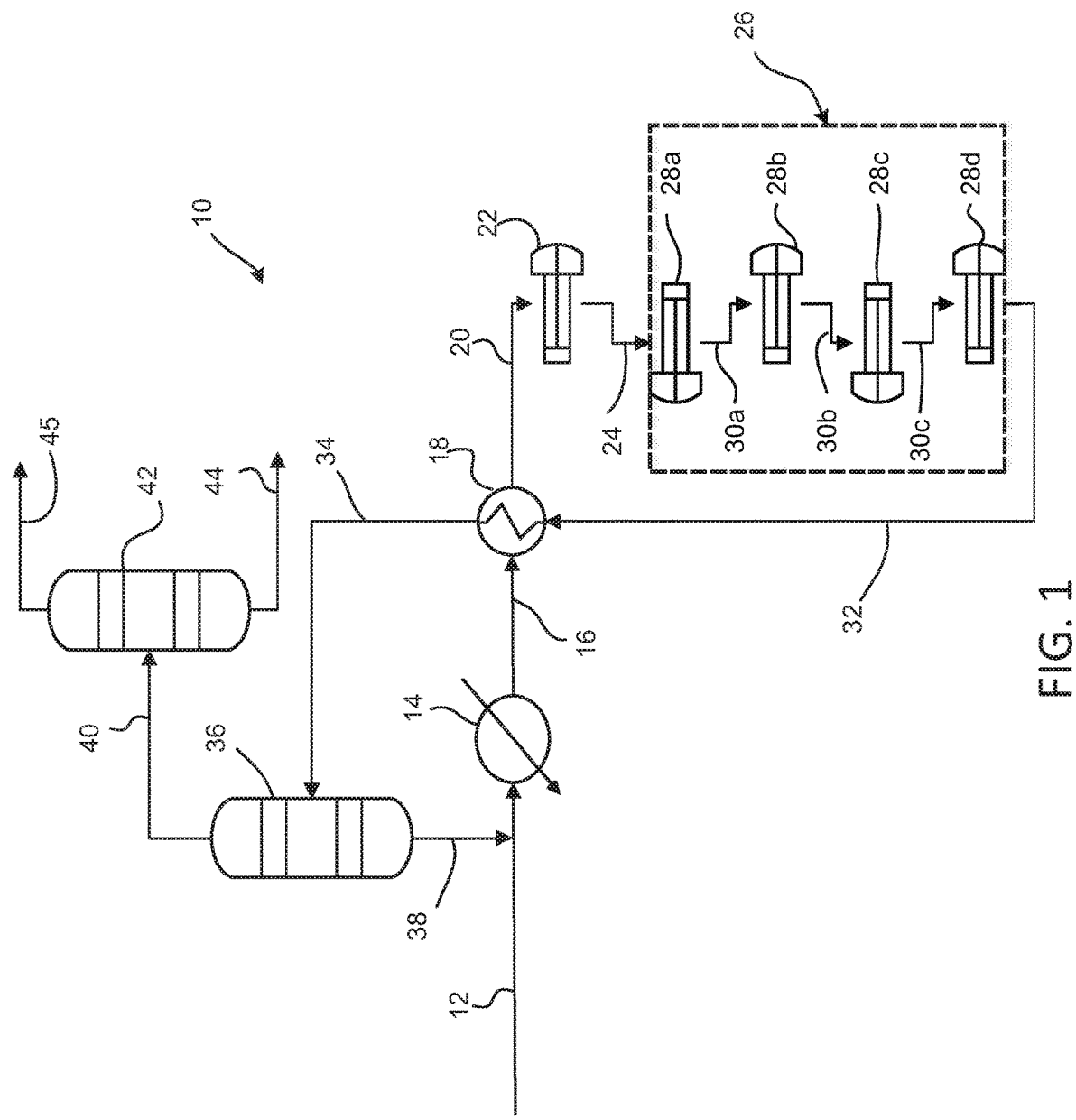
FIG. 1 is a process flow diagram showing a portion of a process for manufacturing 2,3,3,3-tetrafluoropropene, according to some embodiments of this disclosure.

FIG. 1 is a process flow diagram showing Step 3 of a process for manufacturing 2,3,3,3-tetrafluoropropene, according to some embodiments of this disclosure. FIG. 1 shows that a process flow 10 for Step 3 can include a flow of a composition 12 including liquid 244bb flowing into a heater 14. The flow of the composition 12 including liquid 244bb can be from any process according to step 2 above, or from any other source of liquid 244bb. The flow of the composition 12 can also include residues, such as unreacted 1233xf, recycled 1234yf, HF, HCl and minor impurities.

The heater 14 can heat the liquid 244bb to at least its dew point at the process pressure, thereby creating a vaporized flow 16 of 244bb which may be a saturated vapor or a superheated vapor. The process pressure may be subatmospheric or superatmospheric. The process pressure may be a gauge pressure as low as −4 pounds per square inch (psig) (−28 kilopascal (kPa)), 0 psig (0 kPa), 20 psig (138 kPa), 30 psig (207 kPa), or 40 psig (276 kPa), or as high as 80 psig (552 kPa), 110 psig (758 kPa), 150 psig (1,034 kPa), 200 psig (1,379 kPa), or 300 psig (2,068 kPa), or may be within any range defined between any two of the foregoing values, such as −4 psig (−28 kPa) to 300 psig (2,068 kPa), 0 psig (0 kPa) to 200 psig (1,379 kPa), 20 psig (138 kPa) to 150 psig (1,034 kPa), 30 psig (207 kPa) to 110 psig (758 kPa), 40 psig (276 kPa) to 80 psig (552 kPa), 80 psig (552 kPa) to 150 psig (1,034 kPa), or 40 psig (276 kPa) to 110 psig (758 kPa), for example.

The heater 14 can heat, vaporize, and optionally superheat the liquid 244bb to a temperature as low as 40° F. (4° C.), 100° F. (38° C.), 150° F. (66° C.), 200° F. (93° C.), or 250° F. (121° C.), or as high as 300° F. (149° C.), 350° F. (177° C.), 400° F. (204° C.), 450° F. (232° C.), or 500° F. (260° C.), or may be within any range defined between any two of the foregoing values, such as 40° F. (40° C.) to 500° F. (260° C.), 100° F. (38° C.) to 450° F. (232° C.), 150° F. (66° C.) to 400°

F. (204° C.), 200° F. (93° C.) to 350° F. (177° C.), 250° F. (121° C.) to 300° F. (149° C.), or 400° F. (204° C.) to 500° F. (260° C.), for example.

The vaporized flow 16 of 244bb can pass through a heat exchanger 18, to increase a temperature of the vaporized 244bb, creating a superheated, vaporized flow 20 of 244bb. The heat exchanger 18 can be an economizer or interchanger to recover heat from reactor effluent, as described below. The heat exchanger 18 can be a shell and tube heat exchanger, for example. The superheated, vaporized flow 20 of 244bb can pass through a superheater 22 to further increase the temperature of the vaporized 244bb and create a further superheated flow 24 of 244bb. The superheater 22 can be an electric heater as is known in the art, although other types of heaters are also contemplated. The temperature of the further superheated flow 24 of 244bb can be as low as 575° F. (302° C.), 610° F. (321° C.), 650° F. (343° C.), 690° F. (366° C.), 735° F. (392° C.), 780° F. (416° C.), 830° F. (443° C.), 850° F. (454° C.), 870° F. (466° C.), 900° F. (482° C.), 930° F. (499° C.), or 960° F. (516° C.), or as high as 1,040° F. (560° C.), 1,080° F. (582° C.), 1,120° F. (604° C.), 1,160° F. (627° C.), or 1,200° F. (649° C.), or may be within any range defined between any two of the foregoing values, such as 575° F. (302° C.) to 1,200° F. (649° C.), 850° F. (454° C.) to 1,200° F. (649° C.), 870° F. (466° C.) to 1,160° F. (627° C.), 900° F. (482° C.) to 1,120° F. (604° C.), 930° F. (499° C.) to 1,080° F. (582° C.), 960° F. (516° C.) to 1,040° F. (560° C.), or 870° F. (466° C.) to 930° F. (499° C.), for example.

The further superheated flow 24 of 244bb can be provided to a reactor 26. As shown in FIG. 1, the reactor 26, can include a plurality of reactor sections 28a, 28b, 28c, and 28d fluidly connected to each other by reactor flows 30a, 30b, and 30c. Each of the reactor sections 28a, 28b, 28c, 28d can include at least one immersion heater including a heater surface configured to be in contact with the superheated 244bb. Within the reactor 26, the superheated 244bb is brought into contact with the heater surfaces for a contact time during which at least some of the 244bb in the composition is dehydrochlorinated to make 1234yf, and producing HCl as a byproduct (Eq. 1). The contact time can be less than 10 seconds. The contact time can be as short as 0.1 seconds, 0.5 seconds, 1 second, 2 seconds, 3 seconds, or 4 seconds, or as long as 5 seconds, 6 seconds, 7 seconds, 8 seconds, 9 seconds, or 10 seconds, or may be within any range defined between any two of the foregoing values, such as 0.1 second to 10 seconds, 0.5 seconds to 9 seconds, 1 second to 8 seconds, 2 seconds, to 7 seconds, 3 seconds to 6 seconds, 4 seconds to 5 seconds, 0.1 seconds to 9 seconds, or 5 seconds to 9 seconds, for example.

The heater surface can have a surface temperature as low as 850° F. (454° C.) 870° F. (466° C.), 900° F. (482° C.), 940° F. (504° C.), 965° F. (518° C.), 990° F. (532° C.), 1,010° F. (543° C.), or 1030° F. (554° C.), or as high as 1,080° F. (585° C.), 1,110° F. (593° C.), 1,140° F. (616° C.), 1,170° F. (632° C.), or 1,200° F. (649° C.), or may be within any range defined between any two of the foregoing values, such as 850° F. (454° C.) to 1,200° F. (649° C.), 870° F. (466° C.) to 1,200° F. (649° C.), 940° F. (504° C.) to 1,200° F. (649° C.), 965° F. (512° C.) to 1,170° F. (632° C.), 990° F. (532° C.) to 1,140° F. (616° C.), 1,010° F. (543° C.) to 1,110° F. (593° C.), 1,030° F. (554° C.) to 1,080° F. (585° C.), or 965° F. (518° C.) to 1,010° F. (543° C.), for example.

In some embodiments, the heater surface can be a catalytic surface with respect to the reaction scheme shown above in reference to Step 3. In some embodiments, the catalytic surface can include electroless nickel, nickel, stainless steel, nickel-copper alloy, nickel-chromium-iron alloy, nickel-chromium alloy, nickel-chromium-molybdenum alloy, or combinations thereof.

In some other embodiments, the heater surface is not a catalytic surface with respect to the reaction scheme shown above in reference to Step 3. In some embodiments, the heater surface includes gold, platinum, or a combination thereof.

A build-up of carbon deposits, also called coking, on the heater surfaces of the reactor 26, can reduce the heat transfer between the heater surface and the 244bb. The reactor 26 must be taken offline periodically so that the carbon deposits can be removed. A reduction in carbon deposits can reduce the frequency with which the reactor 26 must be taken out of service for cleaning, and increase the uptime and productivity of the reactor 26. It is believed that the carbon deposits can form according to the following reaction scheme:

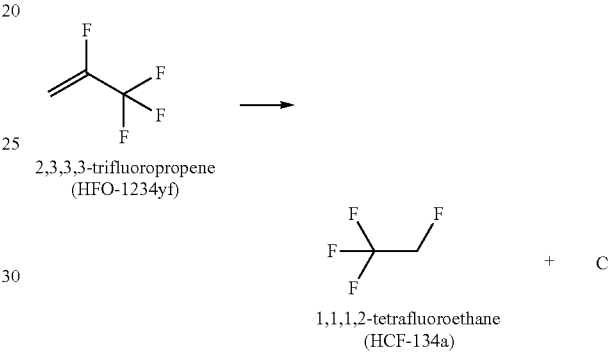

2,3,3,3-trifluoropropene
(HFO-1234yf)

1,1,1,2-tetrafluoroethane
(HCF-134a)

Thus, the extent of carbon formation can be indicated by measuring a concentration of 1,1,1,2-tetrafluoroethane (HFC-134a or 134a) downstream of the reactor 26. A reduction in carbon formation can be indicated by a reduction in the concentration of 134a. It has been surprisingly found that a higher surface temperature, such as from about 975° F. to about 1005° F., in combination with a short contact time, such as less than 10 seconds, can dehydrochlorinate 244bb to make 1234yf while producing fewer carbon deposits. This is unexpected as one skilled in the art would not expect fewer carbon deposits at higher temperatures.

A flow 32 including 1234yf, HCl and unreacted 244bb can flow from the reactor 26 and pass through the heat exchanger 18 to provide additional heat to the vaporized flow 16 of 244bb as described above, and to cool the flow 32 of 1234yf, HCl and unreacted 244bb. A cooled flow 34 of 1234yf, HCl and unreacted 244bb can flow to a distillation column 36 where at least a portion of the unreacted 244bb can be separated from the 1234yf and the HCl, into a recycle flow 38 of unreacted 244bb. In some embodiments, substantially all of the unreacted 244bb can be separated from the 1234yf and the HCl into the recycle flow 38. The recycle flow 38 of unreacted 244bb can join the flow of the composition 12 including 244bb flowing into the heater 14, as shown in FIG. 1.

A flow 40 of the separated 1234yf and HCl can be treated to separate the HCl from the 1234yf by passing through an HCl separation unit 42 to remove the HCl and produce a product stream 44 including the 1234yf. In the embodiment shown in FIG. 1, the HCl separation unit 42 is a distillation tower which produces an anhydrous HCl stream 45, in addition to the product stream 44. In other embodiments, the HCl separation unit 42 may be a falling film type HCl absorber using a recirculating dilute HCl solution and fresh make-up water. In yet other embodiments, the HCl separation unit 42 may be an adiabatic type HCl absorber, as is known in the art. In still other embodiments, the HCl separation unit 42 may be a scrubber using an aqueous, basic solution.

The product stream 1234yf can be a crude product stream including byproducts, such as 3,3,3-trifluoro-1-propyne (TFPY), in addition to the 134a described above, as well as any 244bb not separated into the recycle flow 38. The byproducts can be separated from the 1234yf in the product stream 44 by further processing known in the art (not shown).

In some embodiments, the product stream 44 can include 1234yf at a concentration greater than 99.10 weight percent (wt. %), 99.20 wt. %, 99.30 wt. %, 99.40 wt. %, 99.50 wt. %, 99.60 wt. %, 99.70 wt. %, 99.80 wt. %, 99.90 wt. %, 99.91 wt. %, 99.92 wt. %, or 99.93 wt. %, or greater than any value between any two of the foregoing values.

In some embodiments, the product stream 44 can include 134a at a concentration less than 0.1 wt. %, 0.05 wt. %, 0.02 wt. %, 0.010 wt. %, 0.009 wt. %, 0.008 wt. %, 0.007 wt. %, 0.006 wt. %, 0.005 wt. %, 0.004 wt. %, 0.003 wt. %, 0.002 wt. %, or 0.001 wt. %, or less than any value between any two of the foregoing values. Low values of 134a in the product stream 44 are indicative of low carbon build-up in the reactor 26. It has been found that the carbon build-up in the reactor 26 in the process flow 10 may be reduced by as much as 80% to 90% compared to prior art processes. Reducing the carbon build-up may reduce the reactor downtime and costs associated with required periodic cleaning of the carbon from the reactor 26.

For consistency, the product stream 44 concentrations stated herein are on a 244bb-free basis. That is, any 244bb in the product stream 44 is not included with regard to determining the weight percentages of the 1234yf, 134a, or other component concentrations in the product stream 44.

Figure 2:
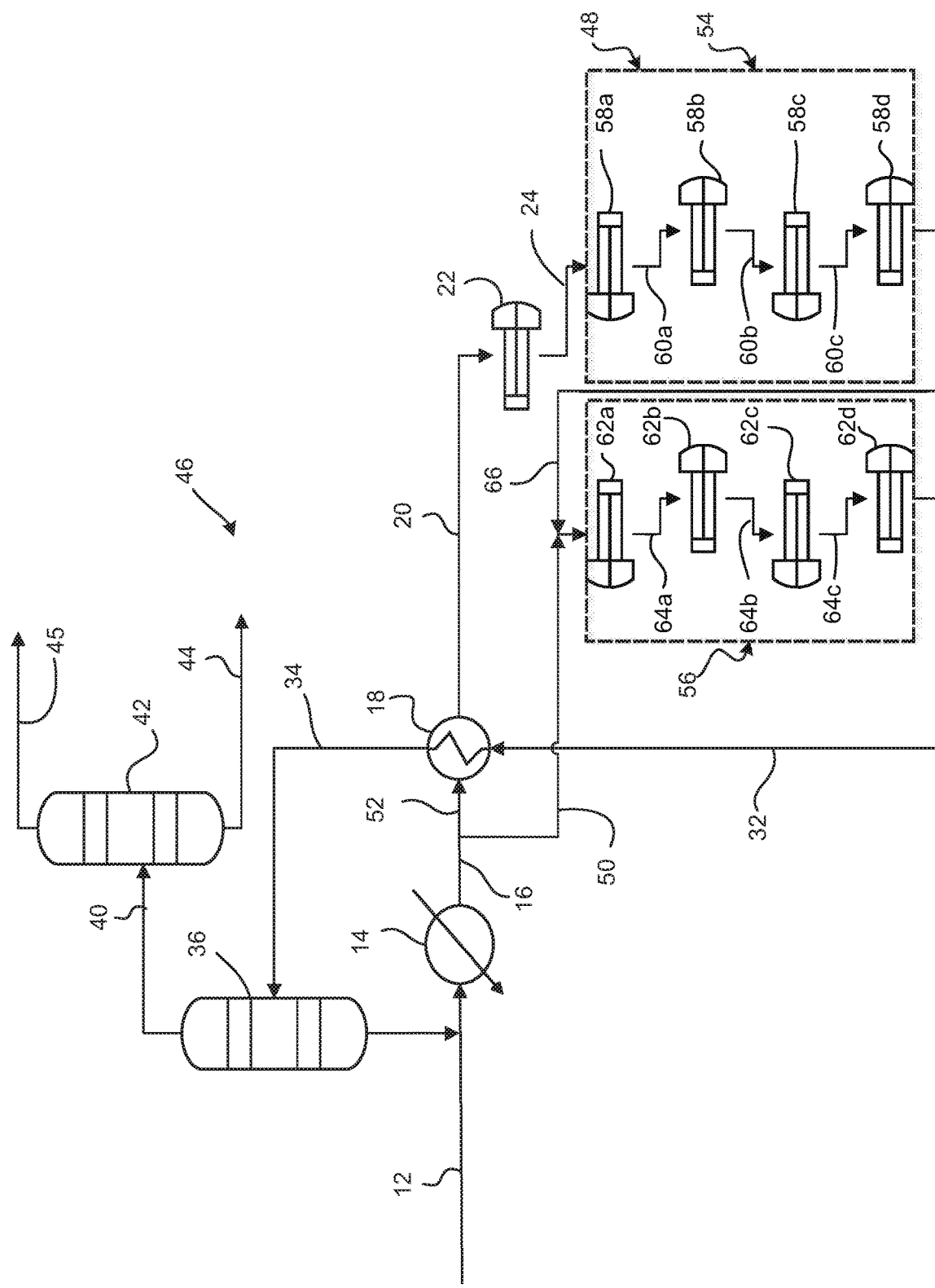
FIG. 2 is a process flow diagram showing a portion of another process for manufacturing 2,3,3,3-tetrafluoropropene, according to some embodiments of this disclosure.

FIG. 2 is a process flow diagram showing Step 3 of another process for manufacturing 2,3,3,3-tetrafluoropropene, according to some embodiments of this disclosure. FIG. 1 shows that a process flow 46 for Step 3 that can be identical to the process flow 10 shown in FIG. 1, except that the reactor 26 is replaced by a two-stage reactor 48, and the vaporized flow 16 of 244bb is divided into a first portion 50 and a second portion 52. The first portion 50 can flow through the heat exchanger 18 as described above for vaporized flow 16 of 244bb in reference to FIG. 1, creating the superheated, vaporized flow 20 of 244bb. The superheated, vaporized flow 20 of 244bb can pass through the superheater 22 to further increase the temperature of the vaporized 244bb and create the further superheated flow 24 of 244bb provided to the reactor 48. The second portion 52 does not flow through the heat exchanger 18 before being provided to the reactor 48.

As shown in FIG. 2, the reactor 48 can include a first stage 54 and a second stage 56. The first stage 54 can include a plurality of reactor sections 58a, 58b, 58c, and 58d fluidly connected to each other by reactor flows 60a, 60b, and 60c. The second stage 56 can include a plurality of reactor sections 62a, 62b, 62c, and 62d fluidly connected to each other by reactor flows 64a, 64b, and 64c. Each of the reactor sections 58a, 58b, 58c, 58d, 62a, 62b, 62c, and 62d can include at least one immersion heater including a heater surface configured to be in contact with the superheated 244bb. As with the reactor 26 described above, within the reactor 48, the superheated 244bb is brought into contact with the heater surfaces for a contact time during which at least some of the 244bb in the composition is dehydrochlorinated to make 1234yf, and producing HCl as a byproduct (Eq. 1). The contact times and temperatures for the process flow 46 can be as described above for the process flow 10.

An interstage flow 66 fluidly connects the first stage 54 to the second stage 56, which is downstream from the first stage 56. The further superheated flow 24 of 244bb from the first portion 50 flows into the first stage 54. The second portion 52 can flow into the second stage 56 along with the interstage flow 66 from the first stage 54, cooling the interstage flow 66 before it enters the second stage 56. The immersion heaters in the second stage reactor sections 62a, 62b, 62c, and 62d may be able to operate at higher heater surface temperatures because of the cooler interstage flow 66 entering the second stage 56. Without wishing to be bound by any theory, it is believed that by operating at higher heater surface temperatures, the conversion of 244bb to 1234yf may be optimized without incurring higher temperatures in the flow including 1234yf, HCl and unreacted 244bb 32 flowing from the reactor 48.

The first portion 50 flowing through the heat exchanger 18 is less than the vaporized flow 16 of 244bb flowing through the heat exchanger 18 as described in FIG. 1, so the temperature of the superheated, vaporized flow 20 of 244bb can be significantly higher than for a given flow 32 including 1234yf, HCl and unreacted 244bb from the reactor 48. The superheater 22 can be reduced in sized because the higher temperature of the superheated, vaporized flow 20 of 244bb may require less heating. A smaller superheater 22 can produce significant capital and operational cost savings.

In some embodiments according to this disclosure, the immersion heaters are electric immersion heaters. In some embodiments, the electric immersion heaters may each be individually controlled, to provide a desired heater surface temperature in different sections of the reactor. In some embodiments, the electric immersion heaters may include tubular bodies enclosing electrical resistance wires which generate heat as an electric current passes through the wires. Such electric immersion heaters may include a ceramic insulating material, such as magnesium oxide, between wires within the same tube to electrically insulate the wires from each other while also conducting heat from the wires to the enclosing tubular body. The exterior surface of the tubular body can form the heater surface, as described above. The ceramic insulating material is also a safety feature. The ceramic insulating material is largely non-reactive with respect to the feeds, products, or byproducts discussed above. Should a leak occur in the tubular body, the ceramic insulating material may prevent further spread of the leak beyond the electric immersion heater, In some embodiments the reactor sections 28a, 28b, 28c, 28d, 58a, 58b, 58c, 58d, 62a, 62b, 62c, and 62d may be shell and tube reactors in which the 244bb flows through the shell, and the tubes are replaced by electric heater elements. In some other embodiments, the reactor sections 28a, 28b, 28c, 28d, 58a, 58b, 58c, 58d, 62a, 62b, 62c, and 62d may be U-tube type reactors with electric flange immersion heaters.

In the embodiments shown in FIGS. 1 and 2, the reactor or reactor stages are illustrated with four sections. However, it is understood that the disclosure includes embodiments having fewer than four sections or more than four sections. It is also understood that embodiments may include two or more reactors in a series configuration and/or in a parallel configuration for dehydrochlorinating 244bb to produce 1234yf.

In the embodiments described above, the heat exchanger 18 is employed to improve the energy efficiency of the process for manufacturing 2,3,3,3-tetrafluoropropene. However, it is understood that some embodiments may not include the heat exchanger 18.

In the embodiments described above, the superheater 22 further superheats the flow of 244bb to the reactor. However, it is understood that some embodiments may not include the superheater 22, relying on the reactor to provide further superheating of the flow of 244bb.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

While this invention has been described as relative to exemplary designs, the present invention may be further modified within the spirit and scope of this disclosure. Further, this application is intended to cover such departures from the present disclosure as come within known or customary practice in the art to which this invention pertains.

EXAMPLES

Example 1

A composition including 96.0 wt. % 244bb, 3.5 wt. % 1233xf and 0.5 wt. % other materials (as measured by gas chromatograph) was vaporized at 70 psig to at least its dew point. The vaporized composition was superheated in a heat exchanger, and then further superheated to 900° F. in a superheater. The further superheated, vaporized composition was introduced into a reactor including four electrically heated sections. The superheater was configured such that the gas velocity was at least twice as high as that in the reactor to minimize coking the in superheater. The heater surface temperature in the reactor was maintained between 993° F. and 997° F. with an average heater surface temperature of 995° F. The superheated, vaporized composition passed through the reactor with an average contact time of 5.46 seconds, based on inlet conditions to the reactor. The reactor output was directed to a distillation column to separate the unreacted 244bb from the 1234yf and HCl. The bottom stream of the distillation output, including the unreacted 244bb, was recovered for recycle. The overhead stream including the 1234yf and HCl was directed to another distillation column to separate HCl as an overhead product and produce a crude product stream including the 1234yf. The process was maintained for 80 hours for an overall conversion of 204bb to 1234yf of 21.3%. The product stream was analyzed by gas chromatograph, using techniques well known in the art. The results are shown in the Table below.

Example 2

A composition including 96.2 wt. % 244bb, 3.6 wt. % 1233xf and 0.2 wt. % other materials (as measured by gas chromatograph) was vaporized at 70 psig to at least its dew point. The vaporized composition was superheated in a heat exchanger, and then further superheated to 900° F. in a superheater. The further superheated, vaporized composition was introduced into a reactor including four electrically heated sections. The superheater was configured such that the gas velocity was at least twice as high as that in the reactor to minimize coking the in superheater. The heater surface temperature in the reactor was maintained between 980° F. and 995° F. with an average heater surface temperature of 988° F. The superheated, vaporized composition passed through the reactor with an average contact time of 5.46 seconds, based on inlet conditions to the reactor. The reactor output was directed to a distillation column to separate the unreacted 244bb from the 1234yf and HCl. The bottom stream of the distillation output, including the unreacted 244bb, was recovered for recycle. The overhead stream including the 1234yf and HCl was directed to another distillation column to separate HCl as an overhead product and produce a crude product stream including the 1234yf. The process was maintained for 92 hours for an overall conversion of 204bb to 1234yf of 20.5%. The product stream was analyzed by gas chromatograph, using techniques well known in the art. The results are shown in the Table below.

Example 3

A composition including 97.6 wt. % 244bb, 2.0 wt. % 1233xf and 0.4 wt. % other materials (as measured by gas chromatograph) was vaporized at 70 psig to at least its dew point. The vaporized composition was superheated in a heat exchanger, and then further superheated to 900° F. in a superheater. The further superheated, vaporized composition was introduced into a reactor including four electrically heated sections. The superheater was configured such that the gas velocity was at least twice as high as that in the reactor to minimize coking the in superheater. The heater surface temperature in the reactor was maintained between 989° F. and 998° F. with an average heater surface temperature of 993.5° F. The superheated, vaporized composition passed through the reactor with an average contact time of 8.4 seconds, based on inlet conditions to the reactor. The reactor output was directed to a distillation column to separate the unreacted 244bb from the 1234yf and HCl. The bottom stream of the distillation output, including the unreacted 244bb, was recovered for recycle. The overhead stream including the 1234yf and HCl was directed to another distillation column to separate HCl as the overhead product and produce a crude product stream including the 1234yf. The process was maintained for 604 hours for an overall conversion of 204bb to 1234yf of 30.3%. The product stream was analyzed by gas chromatograph, using techniques well known in the art. The results are shown in the Table below.

Comparative Example

A composition including 97.9 wt. % 244bb, 1.8 wt. % 1233xf and 0.2 wt. % other materials (as measured by gas chromatograph) was vaporized at 70 psig to at least its dew point. The vaporized composition was heated in a heat exchanger, and then superheated to temperatures ranging from 740° F. to 800° F. in a superheater. The superheated, vaporized composition was introduced into conventional shell and tube reactor, with the reactor tubes containing the composition. The reactor tubes surrounded by a shell containing a heating medium. The bulk temperature inside the reactor tubes was maintained at 900° F., with a surface temperature of the inside of the reactor tubes (in contact with the composition) maintained at about 909° F. The superheated, vaporized composition passed through the reactor with an average contact time of 58 seconds, based on inlet conditions to the reactor. The reactor output was directed to a distillation column to separate the unreacted 244bb from the 1234yf and HCl. The bottom stream of the distillation output, including the unreacted 244bb, was recovered for recycle. The overhead stream including the 1234yf and HCl was directed to another distillation column to separate HCl as an overhead product and produce a crude product stream including the 1234yf. The process was maintained for 396 hours for an overall conversion of 204bb to 1234yf of 29.2%. The product stream was analyzed by gas chromatograph, using techniques well known in the art. The results are shown in the Table below.

TABLE

Gas Chromatograph Results

|        | Example 1     | Example 2     | Example 3     | Comparative Example |
|--------|---------------|---------------|---------------|---------------------|
| 1234yf | 99.922 wt. %  | 99.934 wt. %  | 99.938 wt. %  | 99.946 wt. %        |
| 134a   | 0.0045 wt. %  | 0.0045 wt. %  | 0.0073 wt. %  | 0.0109 wt. %        |
| TFPY   | 0.0563 wt. %  | 0.0365 wt. %  | 0.0354 wt. %  | 0.0190 wt. %        |
| Other  | 0.0172 wt. %  | 0.0250 wt. %  | 0.0193 wt. %  | 0.0241 wt. %        |

As shown in the table, Examples 1-3 from processes having higher heater surface temperatures and shorter contact times produces significantly less 134a, which correlates with significantly less carbon build-up, or coking, in the reactor.

What is claimed is:

1. A process for making 2,3,3,3-tetrafluoropropene (HFO-1234yf), the process comprising:
   providing a composition including at least 96 wt. % 2-chloro-1,1,1,2-tetrafluoropropane (HCFC-244bb);
   vaporizing the composition;
   heating the vaporized composition before providing the composition to a reactor including a heater surface at a surface temperature from about 870° F. (466° C.) to about 1200° F. (649° C.); and
   bringing the composition into contact with the heater surface for a contact time of less than 10 seconds to dehydrochlorinate a portion of the HCFC-244bb to make HFO-1234yf forming a product stream, and
   providing the product stream from the reactor to a distillation column;
     wherein heating the vaporized composition includes exchanging heat between the vaporized composition and the product stream from the reactor before providing the product stream to the distillation column.

2. The process of claim 1, wherein the heater surface is at a surface temperature from about 940° F. (504° C.) to about 1,005° F. (541° C.).

3. The process of claim 2, wherein the HFO-1234yf includes 1,1,1,2-tetrafluoroethane at a concentration less than 0.1 wt. % on an HCFC-244bb-free basis as an indication of a low rate of carbon build-up in the reactor.

4. The process of claim 1, wherein the contact time is from 0.1 seconds to 9 seconds.

5. The process of claim 1, wherein the heater surface includes a catalytic surface.

6. The process of claim 5, wherein the catalytic surface includes electroless nickel, nickel, stainless steel, nickel-copper alloy, nickel-chromium-iron alloy, nickel-chromium alloy, nickel-chromium-molybdenum, or combinations thereof.

7. The process of claim 1, wherein the heater surface is not a catalytic surface.

8. The process of claim 1, further including:
   vaporizing the composition; and
   heating the vaporized composition to a temperature from about 575° F. (302° C.) to 1,200° F. (649° C.) before providing the composition to the reactor.

9. The process of claim 1, wherein the dehydrochlorination of the portion of the HCFC-244bb produces hydrogen chloride (HCl) and wherein the product stream comprises HFO-1234yf, HCl, and unreacted HCFC-244bb, the process further including:
   separating the HFO-1234yf and the HCl from at least a portion of the HCFC-244bb in the distillation column;
   recycling the separated HCFC-244bb forming a recycle stream and combining the recycle stream with the composition forming a combined stream and providing the combined stream into the reactor including the heater surface and vaporizing the combined stream to form a vaporized composition;
   providing the HFO-1234yf and the HCl to an HCl separation unit; and
   separating the HCl from the HFO-1234yf to form a final product stream including the HFO-1234yf.

10. The process of claim 9, wherein the final product stream includes the HFO-1234yf at a concentration greater than 99.1 wt. % on an HCFC-244bb-free basis.

* * * * *